United States Patent [19]

Tate

[11] Patent Number: 4,588,766

[45] Date of Patent: May 13, 1986

[54] ADHESION OF RUBBER TO METALS

[75] Inventor: Philip E. R. Tate, Stockport, England

[73] Assignee: Manchem Limited, Manchesster, England

[21] Appl. No.: 689,191

[22] Filed: Jan. 7, 1985

[30] Foreign Application Priority Data

Jan. 10, 1984 [GB] United Kingdom ............... 8400572

[51] Int. Cl.$^4$ .......................... C08K 3/10; C08J 3/20; C07F 15/04; C07F 15/06
[52] U.S. Cl. ................................. 524/176; 524/184; 524/526; 524/575; 152/450
[58] Field of Search ................... 260/439 R; 524/176, 524/183, 184, 398, 395; 556/7

[56] References Cited

U.S. PATENT DOCUMENTS 4,057,529 11/1977 Leo et al. ........................... 524/184

*Primary Examiner*—Herbert J. Lilling
*Attorney, Agent, or Firm*—James R. Thornton

[57] ABSTRACT

A promoter for improving the adhesion of rubber to metals is obtained by reacting an alkaline earth borate such as calcium borate with a cobalt or nickel carboxylate. Preferred carboxylates contain 3-24 carbon atoms.

14 Claims, No Drawings

ADHESION OF RUBBER TO METALS

This invention relates to adhesion of rubber skim stock to metallic materials, notably coated steel cords, to improve rubber to metal adhesion properties, particularly with regard to resistance to moisture ageing.

Various proposals have been made to improve the adhesion of rubber to metal reinforcement elements embedded therein. For example, brass plating of steel cords has been considered to impart adequate adhesion of the cords to rubber on vulcanization but the presence of exposed steel after cutting of the coated cords provides potential points for weaker adhesion. Further, the plating of steel cord with brass of consistent composition and thickness is difficult and can lead to products on vulcanization having variable bond strengths between the rubber and the reinforcing material. Again, the presence of moisture in the rubber composition is known to affect adversely the adhesion of the metal with the rubber.

Other proposals have suggested various additives which can be ingredients of rubber compositions to promote adhesion of the rubber to metal reinforcements.

British Patent Specification No. 1338930 describes a method for bonding a vulcanizable rubber composition to a metallic material wherein at least one compound, selected from boric acids, metal salts thereof and boric oxide, is incorporated into the composition to improve bonding characteristics.

European Patent application publication No. 0065476 describes a rubber composition containing conventional rubber compounding ingredients and in addition, to improve rubber/metal adhesion, at least one borate or boric acid in conjunction with a crosslinkable monomer containing at least two —CH=CH$_2$ units selected from allyl compounds defined therein. Table 1 in the specification shows that the rubber skim stock includes a cobalt carboxylate.

The use of cobalt and nickel salts of carboxylic acids as direct bond additives for rubber skim stock is well established and a major application is in compounds used for steel cord reinforced tire manufacture. U.S. Pat. No. 4,340,515 describes a solid rubber adhesion promoter composition which comprises 20–90% by weight of cobalt naphthenate, nickel naphthenate or mixture thereof and 10–80% by weight of cobalt resinate, nickel resinate or a mixture thereof.

British Pat. No. 972804 discloses metal-organic compounds which include complex metal-organic compounds based on cobalt and boron, linked through oxygen to the organic component. These compounds, commercially available and known as MANOBOND, are used in rubber compositions to improve their adhesion to metals such as steel, brass or zinc, and have been shown to be more effective than simple cobalt carboxylates with the same concentration of cobalt in the rubber composition. Related compounds are described in British Pat. No. 2022087 which have the added important feature of being able to be produced in the form of easily handled solid products such as free flowing powders or non-agglomerating granules, pastilles or flakes.

Adhesion strength between rubber and metal is known to deteriorate with time due to the corrosion of the metal reinforcement. In the radial tire industry in particular, considerable attention has been drawn to the so-called moisture/corrosion resistance of steel reinforced tires. It is generally accepted that moisture can enter a tire either during manufacture or during its subsequent service life. To a large extent the uptake of moisture in the manufacturing process can be minimised by the use of low moisture content ingredients and also by ensuring that the delay period between compounding and vulcanization is an absolute minimum.

In service, breakdown of a tire can be influenced by a number of factors. Flaws on the surface or within the rubber matrix caused by poor dispersion of the rubber compounding ingredients, inhomogeneous curing or the presence of foreign matter will lead to more rapid failure under conditions of stress. Cracks are formed at the flaws and can lead to possible points of entry of moisture into the tire. The fatigue life of the rubber compound falls after ageing, particularly heat ageing, and the strain exponent often increased due to the thermal oxidation of the vulcanizate. This drop in performance is enhanced in the presence of cobalt containing compounds commonly used as adhesion promoters.

Moisture can also enter the tire through damage which can occur when the tire comes into contact with materials commonly found on road surfaces such as broken glass, nails or gravel. Deep cuts, particularly in the tread region, will expose the steel reinforcement, thus providing a direct channel for the continual ingress of moisture. Once this occurs, conditions are established for attack of the rubber/metal bond. Whilst the action of moisture itself can ultimately lead to tire failure, the rate at which bond failure occurs can also be markedly accelerated by the presence of salt picked up from a road surface.

It is particularly important, that the rubber to steel cord bond is as strong as possible and can be maintained over long periods under adverse ageing conditions as it is expected that radial tires should be able to undergo retreading on several occasions before actual breakdown of the rubber to steel cord bond occurs.

In accordance with the present invention, there is provided an adhesion promoter which comprises the product of the reaction between a cobalt or nickel carboxylate and an alkaline earth borate. The adhesion promoter is used as an ingredient of rubber skim stock and on vulcanization the rubber shows improved bonding characteristics to adjoining metal reinforcements. These improvements are particularly apparent on ageing of the product in the presence of moisture.

The preferred cobalt or nickel carboxylates preferably contain 3–24 carbon atoms which may be represented by propionates, naphthenates, octoates, Versatate and complex carboxylates with boron or phosphorus as for example disclosed in British Patent specification Nos. 972804, 1075125 and 2022087.

Of the alkaline earth borates, which may be selected from magnesium, calcium, strontium and barium borates, calcium borate (CaO.B$_2$O$_3$) is particularly preferred.

The incorporation of an alkaline earth borate into the reaction product of the invention has shown remarkable improvements in the fatigue to failure performance of rubber compositions when compared to similar compositions containing the conventional cobalt salts described in the art.

The reaction product of the invention is manufactured by heating the preformed cobalt or nickel carboxylate at a temperature of between 100°–250° C. in a suitable vessel, adding the finely divided alkaline earth borate and stirring at the elevated temperature until the reaction is completed. On cooling a solid homogeneous product is obtained which can be incorporated as an ingredient in the rubber skim stock prior to being contacted with the metal reinforcement and vulcanization. Prior to cooling, the melt may be processed in various ways, e.g. by pastillation or flaking, so as to obtain the product in a conveniently handleable form.

The preferred reaction products for use as adhesion promoters are manufactured from compositions comprising 1 part of the metal carboxylate and 0.05-1 part alkaline earth metal borate. The rubbers that can be used include natural rubbers and synthetic rubbers such as polybutadiene, polyisoprene, copolymers of butadiene/styrene, isoprene/styrene, EPDM rubbers, polychloroprene and blends thereof. Particularly preferred rubbers are natural rubber and styrene butadiene rubber (SBR).

The rubber skim stock used in the practice of the invention comprises rubber plus conventional rubber compounding ingredients such as pigments, fillers, extenders, accelerators, antioxidants, vulcanizing agents etc. and, as adhesion promotor, 0.2-2 parts by weight per hundred parts rubber (phr) of the reaction product of the invention.

The metal reinforcements to which the rubber is bonded, are normally in the form of steel cords well known as reinforcing elements in the radial tire industry or as reinforcement for conveyor belting and the like. It is preferred that the steel cords are coated or plated with a metal or alloy such as zinc and brass by known methods prior to being incorporated into the rubber compositions.

In the following examples it is shown that improved retention of bond strength is achieved especially on moisture ageing of rubber reinforced with steel cords and the presence of cobalt is less detrimental than known before with regard to the fatigue life of the rubber compositions. Comparison is made between compositions containing the reaction product of the invention and compositions where the metal carboxylate and alkaline earth borate are added as separate ingredients to the skim stock.

EXAMPLE 1

Preparation of Adhesion Promoter

Versatic acid (30.9 Kg) and 2-ethylhexanoic acid (38.1 Kg) were placed in a reaction vessel and mixed by stirring for 10 minutes. Heat was applied and the mixture heated slowly to a temperature of 90° C. An addition of cobalt hydroxide (41.8 Kg) was made over a 15 minutes period followed by propionic acid (35.8 Kg). The temperature was raised gradually to 190° C. while distillation of water of reaction through a Dean & Stark attachment took place.

This temperature was maintained until distillation ceased and a vacuum (minimum 635 mm Hg) had been applied and held for 45 minutes.

The product was cooled to 160° C. and n-butyl orthoborate (33.8 Kg) was added slowly. The mixture was heated to 220° C. and maintained at this temperature until distillation of isobutyl propionate ceased. Vacuum (minimum 635 mm Hg) was applied and held for at least 30 minutes. The product was allowed to cool to 180° C. and an addition of calcium borate (10.4 Kg) was made while stirring. Stirring was continued for 25 minutes then the product was removed from the reaction vessel and allowed to cool.

The final product (115 Kg) was a deep blue brittle solid which could easily be flaked or shaped as desired.

EXAMPLE 2

Preparation of cobalt boroversatate 2-ethylhexanoate (comparative)

Versatic acid (30.9 Kg) and 2-ethylhexanoic acid (38.1 Kg) were placed in a reaction vessel and mixed by stirring for 10 minutes. Heat was applied and the mixture heated slowly to a temperature of 90° C. An addition of cobalt hydroxide (41.8 Kg) was made over a 15 minute period followed by propionic acid (35.8 Kg). The temperature was raised gradually to 190° C. while distillation of water of reaction through a Dean & Stark attachment took place.

This temperature was maintained until distillation ceased and a vacuum (minimum 635 mm Hg) had been applied and held for 45 minutes. The product was cooled to 160° C. and n-butyl orthoborate (33.8 Kg) was added slowly. The mixture was heated to 220° C. and maintained at this temperature until distillation of isobutyl propionate ceased. Vacuum (minimum 635 mm Hg) was applied and held for at least 30 minutes.

The product was cooled to 125° C., then filtered and allowed to cool to room temperature.

The final product (105 Kg) was a deep blue brittle solid which could easily be flaked or shaped as desired.

EXAMPLE 3

A rubber skim stock was prepared having the following composition:

| | |
|---|---|
| Natural rubber | 90 parts by weight |
| Polybutadiene | 10 parts by weight |
| Zinc oxide | 8 parts by weight |
| Stearic acid | 0.5 parts by weight |
| Carbon black HAF | 50 parts by weight |
| Aromatic process oil | 4 parts by weight |
| Flectol H | 1 parts by weight |
| Santoflex 13 | 2 parts by weight |
| Vulkacit DZ | 0.7 parts by weight |
| Insoluble sulphur | 3 parts by weight |

The words Flectol, Santoflex and Vulkacit are Trade Marks.

During blending, skim stock controls (A,B) were prepared by adding 0.625 and 1.08 phr of the product prepared as described in Example 2 which gave 0.16 and 0.3 phr cobalt metal respectively present in the rubber compositions. Skim stock compositions for comparative purposes (C,D) were prepared by adding 0.07 and 0.12 phr of calcium borate to control skim stocks during the blending sequences. Skim stocks were prepared using the adhesion promoter of the invention by incorporating 0.7 and 1.02 phr of the adhesion promoter prepared as described in Example 1 into the basic rubber skim stock identified above (E,F).

Adhesion of the rubber compositions to brass coated steel cords was tested according to ASTM D2229 using an embedment length of 1.27 cm. All compositions were cured for 25 minutes at 153° C.

Results of adhesion tests are given in the following Table 1

TABLE 1

| | Bond Strength Kg/1.27 cm | | | | | |
|---|---|---|---|---|---|---|
| | A | B | C | D | E | F |
| Unaged | 54.0 | 46.4 | 56.0 | 49.1 | 62.0 | 48.4 |

TABLE 1-continued

|  | Bond Strength Kg/1.27 cm | | | | | |
|---|---|---|---|---|---|---|
|  | A | B | C | D | E | F |
| Humidity 3 days Aged | — | 22.8 | — | 19.6 | — | 27.8 |
| RH* = 95  5 days Temp = 83° C. | 47.0 | 15.5 | 48.0 | 16.0 | 53.0 | 23.8 |
| Steam Aged 6½ hours at 121° C. | 45.0 | 13.2 | 46.0 | 15.2 | 55.0 | 21.2 |

*RH means relative humidity

EXAMPLE 4

Cobalt naphthenate (100 parts by weight) was heated to approximately 200° C. and calcium borate (10 parts by weight) was added while stirring. Stirring was continued for 25 minutes before the product was removed from the reaction vessel and allowed to cool.

The product was a deep blue brittle solid.

EXAMPLE 5

During blending of a skim stock of the composition as described in Example 30 a skim stock control was prepared by adding 1.6 phr cobalt naphthenate (G). A skim stock composition for comparative purposes (H) was prepared by adding 0.075 phr calcium borate to a control skim stock during the blending sequence. A skim stock was prepared using an adhesion promoter according to the invention (I) by incorporating 1.675 phr of the product of Example 4 into the basic skim stock.

Adhesion of the rubber compositions to brass coated steel cords was tested according to ASTM D2229 using an embedment length of 1.27 cm. All compositions were cured for 25 minutes at 153° C.

Results of adhesion test are given in the following Table 2.

TABLE 2

|  | Bond Strength Kg/1.27 cm | | |
|---|---|---|---|
|  | G | H | I |
| Unaged | 55.0 | 61.0 | 65.0 |
| Humidity Aged 5 days RH = 95 Temp. = 83° C. | 41.0 | 43.0 | 47.0 |
| Steam Aged 6½ hours at 121° C. | 40.0 | 41.0 | 46.0 |

EXAMPLE 6

A rubber skim stock was prepared having the following composition:

|  | phr |
|---|---|
| Premasticated SMR 10 | 100 |
| N 326 Black | 55 |
| Silica VN 3 | 10 |
| Zinc Oxide | 8 |
| Dutrex* 729 | 3 |
| Escorez* Resin 1102 B | 3 |
| Stearic Acid | 0.5 |
| Santoflex* 13 | 2.0 |
| 80% Insoluble Sulphur in Oil (Crystex* OT 20) | 5.0 (4.0 phr Sulphur) |
| Santocure* MOR | 0.7 |

*Trade marks

A skim stock composition for comparative purposes (J) was prepared by adding 1.0 phr of cobalt boroversatate 2-ethylhexanoate approximately half way through the blending sequence which gave 0.16 phr cobalt metal. A skim stock using an adhesion promoter of the invention (K) similarly prepared by incorporating 0.7 phr of the product prepared according to Example 1 to give 0.16 phr cobalt metal. A control skim stock was prepared using no cobalt additives (L).

Adhesion tests were carried out using a modified static block pull out test based on ASTM D2229(1). Adhesion values are quoted in Kg/cm, the measured pull out force (Kg) being divided by the block width (2.54 cm).

Two standard commercial grades of brass coated steel cords used in tires, were used.

1. Construction 7×4×0.175+1×0.15 with an approximate copper:zinc ratio of 67:33.
2. Construction 3+9+15×0.175+1×0.15 with a lower copper content, the approximate copper:zinc ratio of 63:37.

The results obtained are shown in Table 3.

TABLE 3

|  | J | K | L |
|---|---|---|---|
| 67:33 Brass | | | |
| Unaged | 64.2 | 60.6 | 63.0 |
| Aged: | | | |
| in steam/air. 40 hrs at 120° C. | 40.9 | 46.5 | 19.7 |
| in oxygen bomb 6.9 Bar. 70° C. 48 hrs | 41.3 | 42.1 | 30.7 |
| 5% salt soln. 48 hrs. at 90° C. | 11.0 | 18.9 | 15.0 |
| 10% salt soln. 14 days at R.T. | 17.3 | 19.3 | 9.1 |
| in air at 85° C. 10 days | 49.6 | 50.0 | 43.7 |
| in 95% R.H. at 80° C. 5 days | 31.1 | 37.4 | 19.7 |
| 64:37 Brass | | | |
| Unaged | 60.6 | 63.8 | 61.8 |
| Aged: | | | |
| in steam/air. 40 hrs at 120° C. | 47.2 | 49.2 | 33.5 |
| in oxygen bomb 6.9 Bar. 70° C. 48 hrs | 38.6 | 39.4 | 29.5 |
| 5% salt soln. 48 hrs at 90° C. | 11.9 | 14.2 | 13.0 |
| 10% salt soln. 14 days at R.T. | 9.8 | 9.4 | 9.4 |
| in air at 85° C. 10 days | 51.6 | 50.0 | 50.0 |
| in 95% R.H. at 80° C. 5 days | 42.5 | 56.7 | 57.1 |

Overcure occurs almost inevitably in certain parts of the tire and these parts also reach the highest temperatures. In order to ascertain the affects of overcure on these adhesion systems, test samples were cured to 3 times T 90% plus 5 minutes at 180° C. and tested as before.

The results are shown in Table 4.

TABLE 4

|  | J | K |
|---|---|---|
| 67:33 Brass | | |
| Unaged | 48.8 | 50.8 |
| Aged: | | |
| in steam/air. 40 hrs at 120° C. | 21.3 | 26.4 |
| in oxygen bomb 6.9 Bar. 70° C. 48 hrs | 30.3 | 31.5 |
| 5% salt soln. 48 hrs at 90° C. | 32.3 | 41.7 |
| 10% salt soln. 14 days at R.T. | 41.3 | 44.9 |
| in air at 85° C. 10 days | 42.5 | 45.7 |
| in 95% R.H. at 80° C. 5 days | 26.8 | 35.0 |
| 63:37 Brass | | |
| Unaged | 54.7 | 53.4 |
| Aged: | | |
| in steam/air. 40 hrs at 120° C. | 35.8 | 30.3 |
| in oxygen bomb 6.9 Bar. 70° C. 48 hrs | 27.6 | 35.8 |
| 5% salt soln. 48 hrs at 90° C. | 44.5 | 40.2 |
| 10% salt soln. 14 days at R.T. | 43.7 | 45.7 |
| in air at 85° C. 10 days | 43.7 | 48.8 |
| in 95% R.H. at 80° C. 5 days | 35.0 | 39.4 |

Fatigue to failure measurements at 100% extension were made and the results are shown in Table 5.

TABLE 5

| Fatigue to failure at 100% Extension | | | |
|---|---|---|---|
|  | J | K | L |
| Unaged | | | |
| Kcs. to failure, mean | 116 | 133 | 130 |
| Aged 5 days at 85° C. | | | |
| Kcs. to failure, mean | 35 | 55 | 62 |

What is claimed is:

1. A rubber adhesion promoter consisting essentially of the reaction product of an alkaline earth borate and a cobalt or nickel carboxylate.

2. A promoter according to claim 1 in which said alkaline earth borate is calcium borate.

3. A promoter according to claim 1 in which said carboxylate contains 3 to about 24 carbon atoms.

4. A promoter according to claim 1 in which the ratio of carboxylate to borate is about 1:0.05-1, part by weight.

5. A promoter according to claim 1 which is the reaction product of calcium borate with cobalt carboxylate in which said carboxylate contains 3-24 carbon atoms.

6. A promoter according to claim 1 which is the reaction product of calcium borate with nickel carboxylate in which said carboxylate contains 3-24 carbon atoms.

7. A rubber stock comprising rubber and about 0.2 to 2 parts by weight per hundred parts rubber of an adhesion promoter according to claim 1.

8. The method for producing a rubber adhesion promoter comprising reacting an alkaline earth borate with a cobalt or nickel carboxylate.

9. The method according to claim 8 in which said alkaline earth borate is calcium borate.

10. The method according to claim 8 in which said carboxylate contains 3 to about 24 carbon atoms.

11. The method according to claim 8 in which said reaction is at a temperature of about 100° to 250° C.

12. The method according to claim 8 in which about 1 part of said carboxylate is reacted with about 0.05-1 part of said borate.

13. The method according to claim 10 in which said carboxylate is cobalt carboxylate.

14. The method according to claim 10 in which said carboxylate is nickel carboxylate.

* * * * *

UNITED STATES PATENT AND TRADEMARK OFFICE
CERTIFICATE OF CORRECTION

PATENT NO. : 4,588,766
DATED : May 13, 1986
INVENTOR(S) : Philip E.R. Tate

It is certified that error appears in the above-identified patent and that said Letters Patent is hereby corrected as shown below:

Column 4, line 55, the number "1.02" should read -- "1.20" --.
Column 5, line 23, the number "30" should read -- "3" --.
Column 6, line 30, the number "64:37" should read -- "63:37" --.

Signed and Sealed this

Twenty-ninth Day of July 1986

[SEAL]

Attest:

DONALD J. QUIGG

Attesting Officer

Commissioner of Patents and Trademarks